United States Patent

Sato et al.

[11] Patent Number: 4,714,764
[45] Date of Patent: Dec. 22, 1987

[54] 2-(4-PYRIDYLAMINOMETHYL)-BENZIMIDAZOLE DERIVATIVES HAVING ANTIVIRAL ACTIVITY

[75] Inventors: Nobukatsu Sato, Nara; Haruo Kuraiyama, Mukou; Masanobu Agou, Ikeda, all of Japan

[73] Assignee: Maruishi Seiyaku Kabushiki Kaisha, Osaka, Japan

[21] Appl. No.: 884,624

[22] Filed: Jul. 11, 1986

[30] Foreign Application Priority Data

Jul. 15, 1985 [JP] Japan ................. 60-156680

[51] Int. Cl.⁴ .......................... C07D 401/02
[52] U.S. Cl. .................................... 546/271
[58] Field of Search ........................ 546/272

[56] References Cited
PUBLICATIONS

Chem. Abstracts, vol. 98, Abst. No. 98:46775h, 1983.

Chem. Abstracts, vol. 45, Abst. No. 45:1116g, 1951.

Primary Examiner—Henry R. Jiles
Assistant Examiner—Zinna Northington
Attorney, Agent, or Firm—Wenderoth, Lind & Ponack

[57] ABSTRACT

Provided herein is an antiviral 2-(4-pyridylaminomethyl)-benzimidazole of the formula:

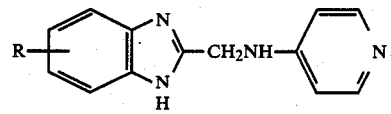

wherein R is a radical selected from the groups consisting of hydrogen, short-chain alkyl, short-chain alkoxy, benzoyl, halogenomethyl, halogen, nitro and amino groups; the preparation of these compounds and antiviral composition containing such compounds.

2 Claims, No Drawings

2-(4-PYRIDYLAMINOMETHYL)-BENZIMIDAZOLE DERIVATIVES HAVING ANTIVIRAL ACTIVITY

BACKGROUND OF THE INVENTION (a) Field of the invention

This invention relates to 2- (4- pyridylaminomethyl)-benzimidazole derivatives represented by the following formula:

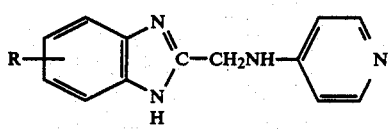

wherein R is a radical selected from the group consisting of hydrogen, short-chain alkyl, short-chain alkoxy, benzoyl, halogenomethyl, halogen, nitro and amino group, and to the preparation thereof.

(b) Description of the prior art

Since benzimidazole derivatives were reported to show antiviral activity by R. L. Thompson [The Journal of Immunology Vol. 55, 345 (1947)], synthesis and biological evaluation of a large number of this series of the compound has been reported. Especially, 2-(anilinomethyl)-benzimidazole represented by the following formula:

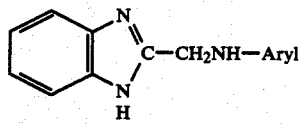

has been recorded in Chemical Abstracts (Vol. 50, 3906f), and its derivatives have been shown to exhibit biological activity [Mizuno et al; Yakugaku Zasshi: 85, 926–955(1965)]

Picornavirus infections are regarded as the most common viral infections in man. This family of viruses consists of the enteroviruses and rhinoviruses. The enteroviruses cause a broad spectrum of clinical illnesses ranging from eruption, hemorrhagic conjunctivitis and mild upper respiratory ailments to more severe disease such as aseptic meningitis, myocarditis, poliomyelitis, etc. Generally, enterovirus infections of the pediatric population result in greater morbidity and mortality. Recent studies have shown that relatively mild pediatric infections can result in long-term neurological sequelae. Rhinoviruses are responsible for 50% of the common cold infections and cause mild localized infections of the upper respiratory tract.

Since the result of serological testing indicated that there are at least 70 serotypes of rhinovirus and enterovirus, prophylaxis by vaccine has not been practical or effective except for polioviruses. Therefore, chemotherapy against picornavirus infection deserves serious consideration.

In view of above mention, we synthesized 2-(4- pyridylaminomethyl)-benzimidazole and its derivatives, and could demonstrate antipicornavirus activity of these compounds.

DETAILED DESCRIPTION OF THE INVENTION

At first, the positions on a benzimidazole ring are numbered as per the following formula:

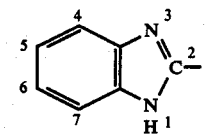

$N^1$ has a tautomeric relation with $N^3$ and $C^5$ has the same relation with $C^6$ and $C^4$ has the same relation with $C^7$. Consequently, it is permitted to express any substituent located on the 5- position of the above ring as the manner of 5(6), and such a manner of expression manner will be followed in this specification.

Some of the promising compounds of this invention will be listed as follows:

(I) 2- (4- pyridylaminomethyl) benzimidazole dihydrochloride (II) 2- (4- pyridylaminomethyl)-5(6)-chlorobenzimidazole dihydrochloride (III) 2- (4- pyridylaminomethyl)-5(6)-benzoylbenzimidazole dihydrochloride (IV) 2- (4- pyridylaminomethyl)-5(6)-methoxybenzimidazole dihydrochloride (V) 2- (4- pyridylaminomethyl)-5(6)-methylbenzimidazole dihydrochloride (VI) 2- (4- pyridylaminomethyl)-5(6)-nitrobenzimidazole dihydrochloride (VII) 2- (4- pyridylaminomethyl)-5(6)-dichlorobenzimidazole dihydrochloride (VIII) 2- (4- pyridylaminomethyl)-5(6)-aminobenzimidazole trihydrochloride (IX) 2- (4- pyridylaminomethyl)-5(6)-trifluoromethylbenzimidazole dihydrochloride (X) 2- (4- pyridylaminomethyl)-5(6)-ethylbenzimidazole dihydrochloride (XI) 2- (4- pyridylaminomethyl)-4(7)-methylbenzimidazole dihydrochloride (XII) 2- (4- pyridylaminomethyl)-5,6- dimethylbenzimidazole dihydrochloride

METHOD OF SYNTHESIS

Example 1 (Compound I)

(a) Preparation of the starting material (2-chloromethylbenzimidazole)

It is a known compound and can be obtained from the reaction of 0-phenylenediamine and monochloroacetic acid.

(b) Preparation of 2- (4- pyridilaminomethyl)benzimidazole dihydrochloride

A solution of 1.665 g (10 m mol) of 2- chloromethybenzimidazole and 1.88 g (20 m mol) of 4- aminopyridine in 20 ml of ethanol was refluxed under heating for three hours. The solution was evaporated in vacuo to a dark oil, dissolved in 20 ml of water and washed twice with 20 ml of ethylacetate The aqueous phase was evaporated in vacuo. The residual oil was dissolved in 3 ml of concentrated hydrochloric acid and chilled (0° C.) causing a crystalline precipitate to form. The crystals were filtered with the aid of ethanol. Recrystallization from methanol gave 1.68 g (53.3%) of the title compound (I).

Analysis for $C_{13}H_{12}N_4.2HCl.H_2O$: Found C:49.93; H:5.17; N:1708; Calcd C:49.53; H:5.12; N:17.78

Example 2 (Compound IV)

(a) Preparation of 2-chloromethyl-5(6)-methoxybenzimidazole hydrochloride

In 12.15 ml of 3N aqueous hydrochloric acid were added 2.1 g (12 m mol) of 4- methoxy-1,2-phenylenediamine hydrochloride and 1.3 g (17 m mol) of glycolic acid, and the mixture was heated at 120° C. for an hour. The reaction solution was cooled to room temperature, and rendered alkaline by the addition of ammonium hydroxide. The solution was filtered under suction, and the precipitate was washed with water and dried to give 2-hydroxymethyl-5(6)-methoxy-benzimidazole. This yellow solid 1 g (5.6 m mol) was added to a stirred solution of 0.75 g (0.46 ml, 63 m mol) of thionyl chloride in 10 ml of dry chloroform under cooling with ice and then, the mixture was refluxed for 2 hours. After cooling, to the reaction ethanol was added dropwise to decompose the excess thionyl chloride and evaporated to dryness.

The residual solid was triturated with 30 ml of petroleum ether and washed with 20 ml of chloroform to yield 1.24 g (44.3%) of the title compound as reddish violet crystals: mp. 187°–191° C.

Analysis for $C_9H_9N_2OCl.HCl$: Found C:46.96; H:4.76; N:12.07; Calcd C:46.37; H:4.32; N:12.02

(b) Preparation of 2-(4-pyridylaminomethyl)-5(6)-methoxybenzimidazole dihydrochloride A solution of 1.22 g (5.2 m mol) of 2-chloromethyl-5(6)-methoxybenzimidazole hydrochloride was obtained from procedures as described above, in 30 ml of methanol was stirred overnight with 0.53 g of sodium bicarbonate. Then, a crystalline precipitate was filtered off and the filtrate was evaporated in vacuo. The residue and 0.97 g (10.3 m mol) of 4-aminopyridine were dissolved in 10 ml of ethanol and refluxed for 3 hours. After cooling, the reaction solution was filtered and the filtrate was evaporated in vacuo. The residual oil was dissolved in 10 ml of water and washed twice with 20 ml of ethyl acetate. The aqueous phase was evaporated to dryness. The residual oil was dissolved in 1.5 ml of concentrated hydrochloric acid and chilled (0° C.) causing a crystalline precipitate to form. The crystals were filtered with the aid of 30 ml of ethanol.

Recrystallization from a mixture solution of methanol and ethanol gave 0.9 g (48.86%) of the title compound (IV) as white crystals.

Example 3 (compound VII)

(a) Preparation of 2-chloromethyl-5,6-dichlorobenzimidazole

A solution of 1.77 g (10 m mol) of 4,5-dichloro-1,2-phenylenediamine in 15 ml of 4N aqueous hydrochloric acid was stored at room temperature overnight. To the solution was added 1.42 g (15 m mol) of monochloroacetic acid, and refluxed for 3 hours and filtered. The filterate was cooled to room temperature, stirred and rendered alkaline by addition of ammonium hydroxide. The separated precipitate was washed with water and dried to give 1.9 g (68%) of the title compound.

(b) Preparation of 2-(4- pyridyl aminomethyl)-5,6-dichlorobenzimidazole dihydrochloride A solution of 1.0 g (4.2 m mol) of 2- chloromethyl-5,6-dichlorobenzimidazole and 1.19 g (12.6 m mol) of 4-aminopyridine in 15 ml of ethanol was refluxed for 5 hours. The reaction solution was cooled to room temperature and evaporated in vacuo. The residual oil was crystallized from acetone. The precipitate was dissolved in a little methanol, added 2 ml of concentrated hydrochloric acid and chilled (0° C.) causing a crystalline precipitate to form. This precipitate was filtered and dried to give 0.55 g (35.77%) as creamy crystals.

Analysis for $C_{13}H_{10}N_4Cl_2.2HCl$: Found C:42.17; H:3.29; N:15.12; Calcd C:42.65; H:3.30; N:15.31

Example 4 (Compound IX)

(a) Preparation of 4- trifluoromethyl-1,2-phenylene diamine

A solution of 6.18 g (30 m mol) of 4-amino-3-nitrobenzotrifluoride in 150 ml of ehtanol was hydrogenated at atmospheric pressure over 1.5 g of 5% Pd/C with Ishii's Catalytic Hydrogenation Apparatus with Magnetic Stirrer Model CHA-M. The catalyst was filtered off. The filterate was evaporated and the residue was crystallized from petroleum ether to give 4.5 g (85.17%) as white crystals.

(b) Preparation of 2-chloromethyl-5(6)-trifluoromethylbenzimidazole

To a solution of 3 g (17.0 m mol) of 4-trifluoromethyl-1,2-phenylenediamine in 17 g (68.1 m mol) of 4N aqueous hydrochloric acid was added 2.4 g (25.5 m mol) of monochloroacetic acid and refluxed for 2 hours. The reaction solution was cooled to room temperature and rendered alkaline by addition of ammonium hydroxide. The separated precipitate was washed with water and dried to give 2.7 g (67.56%).

(c) Preparation of 2- (4-pyridylaminomethyl)-5(6)-trifluoromethylbenzimidazole dihydrochloride.

A solution of 2 g (9 m mol) of 2- chloromethyl-5(6)-trifluoromethylbenzimidazole, 1.7 g (18 m mol) of 4-aminopyridine and 1.8 g (18 m mol) of triethylamine in 30 ml of ethanol was refluxed for 5 hours. The reaction solution was evaporated in vacuo, dissolved in 20 ml of water, and adjusted the pH to the range from 5–7 with concentrated hydrochloric acid. The solution was washed twice with 20 ml of ethyl acetate.

The aqueous phase was evaporated in vacuo. The residue was added 2.25 g (22.5 m mol) of concentrated hydrochloric acid and dried in vacuo, that crystallized from ethanol to give 1.05 g (31.99%) as white crystals.

Example 5 (Compound X)

(a) Preparation of 4- ethyl-2-nitroaniline

According to the method of synthesis for 2-amino-3-nitrotoluene (Organic Syntheses Collective Volume IV P.42–45) 6 g of 4- ethylaniline was added dropwise to 30 ml of acetic anhydride and then, the mixture was treated dropwise with 6.3 ml (100 m mol) of 70% nitric acid at 12°–13° C. After the mixture was stirred for some time at 10°–12° C., the reaction solution was poured into an ice water. Oily product was separated and heated with 15 ml of concentrated hydrochloric for one hour. The reaction solution was alkaline with dilute aqueous sodium hydroxide and then, partitioned with 100 ml of chloroform. The organic layer was washed with water and dried on anhydrous sodium sulfate. Removal of the solvent in vacuo gave 5.76 g (69.32%) of 4-ethyl-2-nitroaniline.

(b) Preparation of 4-ethyl-1,2-phenylenediamine

A solution of 5.7 g (34.3 m mol) of 4-ethyl-2-nitroaniline in 150 ml of ethanol was hydrogenated at atmospheric pressure over 1.8 g of 5% Pd/C with Ishii's Catalytic Hydrogenation Apparatus with Magnetic Stirrer Model CHA-M. The catalyst was filtered off, and removal of the solvent in vacuo gave an oil (4 g). Then, 6 g (58.8 m mol) of concentrated hydrochloric acid was added to the solution, that gave 5.4 g (75.33%) of 4-ethyl-1,2-phenylenediamine dihydrochloride.

(c) Preparation of 2-chloromethyl-5(6)-ethylbenzimidazole

To a solution of 2 g (9.6 m mol) of 4-ethyl-1,2-phenylenediamine dihydrochloride in 10 ml of 4N aqueous hydrochloric acid was added 1.36 g (14.4 m mol) of monochloroacetic and refluxed for 3 hours. After cooling, the reaction solution was made slightly alkaline with ammonium hydroxide. After filtration of the solid, it was washed with water to yield 1.8 g (96.77%) of 2-chloromethyl-5(6)-ethylbenzimidazole.

(d) Preparation of 2- (4- pyridylaminomethyl)-5(6)-ethylbenzimidazole

To a solution of 1.5 g (7.7 m mol) of 2- chloromethyl-5(6)-ethylbenzimidazole in 30 ml of ethanol was added 1.45 g (15.4 m mol) of 4-aminopyridine and refluxed for 2 hours. After the reaction mixture was evaporated in vacuo, the residue was dissolved in 20 ml of water and washed twice with 20 ml of ethyl acetate. The aqueous phase was evaporated in vacuo. Then, the residue was dissolved 2.1 g (21 m mol) of concentrated hydrochloric acid and crystallized from ethanol to produce 0.8 g (31.94%) of 2- (4- pyridylaminomethyl)-5(6)-ethylbenzimidazole dihydrochloride as white crystals.

Analysis for $C_{15}H_{16}N_4.2HCl.H_2O$: Found C:52.09; H:5.82; N:16.06; Calcd C:52.44; H:5.54; N:16.32

Example 6 (Compound XI)

(a) Preparation of 3-methyl-1,2-phenylenediamine

A solution of 4.56 (30 m mol) of 2-methyl-6-nitroaniline in 150 ml of methanol was hydrogenated at atmospheric pressure over 0.9 g of 5% Pd/C with Ishii's Catalytic Hydrogenation Apparatus with Magnetic Stirrer Model CHA-M. The catalyst was filtered off. The solvent was evaporated, and the residue was crystallized from petroleum ether to give 3.25 g (88.67%) as gray crystals.

(b) Preparation of 2-chloromethyl-4-methylbenzimidazole

A solution of 1.83 g (15 m mol) of 3-methyl-1,2-phenylenediamine in 20 ml of 4N aqueous hydrochloric acid was stored at room temperature overnight. To the solution was added 2.13 g (22.5 m mol) of monochloroacetic acid and refluxed for 3 hours. The reaction solution was cooled to room temperature, rendered alkaline by addition of ammonium hydroxide and extracted with ethyl acetate. The ethyl acetate layer was washed with water and dried on anhydrous sodium sulfate. The solvent was evaporated in vacuo and the residue was crystallized from ethyl ether to give 0.8 g (29.52%).

(c) Preparation of 2- (4-pyridylaminomethyl)-4(7)-methylbenzimidazole dihydrochloride A solution of 0.7 g (3.88 m mol) of 2-chloro-4-methylbenzimidazole and 0.73 g (7.75 m mol) of 4-aminopyridine in 10 ml of ethanol was refluxed for 3 hours. The reaction solution was cooled to room temperature and filtered. Thereafter the filtrate was evaporated in vacuo, the residue was dissolved in water and washed several times with ethyl acetate. The aqueous phase was evaporated in vacuo. The residual oil was added 2 ml of of concentrated hydrochloric acid and dried in vacuo, that crystallized from ethanol to give 0.25 g (27.47%).

Analysis for $C_{14}H_{14}N_4.2HCl.H_2O$: Found C:51.99; H:5.42; N:17.19; Calcd C:51.09; H5.51; N:17.02

The physical properties of the representative compounds of this invention will be listed below:

Compound I

Formula: $C_{13}H_{12}N_4.2HCl.H_2O$
Melting point: 195°–197° C.
IR $\nu$max cm$^{-1}$: 1650, 1540, 1190, 750, 650
$^1$H-NMR (D$_2$O, DMSO-d$_6$)$\delta$: 6.0 (2H), 7.0 (2H), 7.4–7.9 (4H), 8.4 (2H)

Compound II

Formula: $C_{13}H_{11}N_4Cl.2HCl.H_2O$
Melting point: 262°–265° C.
IR $\nu$max cm$^{-1}$: 1660, 1540, 1190
$^1$NMR (D$_2$O, DMSO-d$_6$)$\delta$: 5.9 (2H), 7.0 (2H), 7.3–7.9 (3H), 8.4 (2H)

Compound III

Formula: $C_{20}H_{16}N_4 O.2HCl.H_2O$
Melting point: 163°–168° C.
IR $\nu$max cm$^{-1}$: 1660, 1640, 1530, 1280, 1180, 840, 700
$^1$HNMR (D$_2$O, DMSO-d$_6$)$\delta$: 5.8 (2H), 7.0 (2H), 7.5–8.0 (8H), 8.4 (2HO Compound IV Formula: $C_{14}H_{14}N_4 O.2HCl.1.5H_2O$
Melting point: 196°–199° C.
IR $\nu$max cm$^{-1}$: 1660, 1540, 1200, 840
$^1$H-NMR (D$_2$O, DMSO-d$_6$)$\delta$: 3.9 (3H), 6.0 (2H), 7.0 (2H), 7.2 (2H), 7.7 (1H), 8.4 (2H)

Compound V

Formula: $C_{14}H_{14}N_4.2HCl.H_2O$
Melting point: 199°–203° C.
IR $\nu$max cm$^{-1}$: 1650, 1540, 1200, 830
$^1$H-NMR (D$_2$O, DMSO-d$_6$)$\delta$: 2.5 (3H), 6.0 (2H), 7.0 (2H), 7.2–7.8 (3H), 8.4 (2H)

Compound VI

Formula: $C_{13}H_{13}N_5O_2.2HCl$
Melting point: >300° C.
IR $\mu$max cm$^{-1}$: 1650, 1520, 1340, 1210, 830
$^1$H-NMR (D$_2$O, DMSO-d$_6$)$\delta$: 5.9 (2H), 7.0 (2H), 7.7–8.6 (3H)

Compound VII

Formula: $C_{13}H_{10}N_4Cl_2.2HCl$
Melting point: >300° C.
IR $\nu$max cm$^{-1}$: 1650, 1540, 1190, 840 $^1$H-NMR (D$_2$O, DMSO-d$_6$)$\delta$: 5.8 (2H), 7.0 (2H), 7.9 (2H), 8.3 (H)

Compound VIII

Formula: $C_{13}H_{13}N_5.3HCl$
Melting point: 217°–222° C.
IR νmax cm$^{-1}$: 3360, 3160, 1160, 850, 600
$^1$H-NMR (D$_2$O, DMSO-d$_6$)δ: 5.9 (2H), 7.0 (2H), 7.4–7.6 (1H), 7.8–8.0 (2H), 8.2 (2H)

Compound IX

Formula: $C_{14}H_{11}N_4F_3.2HCl$
Melting point 154°–156° C.
IR νmax cm$^{-1}$: 1660, 1330, 1200, 1130, 820
$^1$H-NMR (D$_2$O, DMSO-d$_6$)δ: 5.9 (2H), 7.0 (2H), 7.6–8.1 (3H), 8.3 (2H)

Compound X

Fromula: $C_{15}H_{16}N_4.2HCl.H_2O$
Melting point: 185°–188° C.
IR νmax cm$^{-1}$: 1650, 1540, 1200, 830
$^1$H-NMR (D$_2$O, DMSO-d$_6$)δ: 1.2 (3H), 2.8 (2H), 6.0 (2H), 7.0 (2H), 7.3–7.9 (3H), 8.3 (2H)

Compound XI

Fromula: $C_{14}H_{14}N_4.2HCl.H_2O$
Melting point: 230°–237° C.
IR νmax cm$^{-1}$: 1640, 1530, 1180, 840, 780, 740
$^1$H-NMR (D$_2$O, DMSO-d$_6$)δ: 2.6 (3H), 6.0 (2H), 7.0 (2H), 7.1–7.7 (3H), 8.5 (2H)

Compound XII

Formula: $C_{15}H_{16}N_4.2HCl$
Melting point: 295°–298° C.
IR νmax cm$^{-1}$: 1650, 1540, 1180, 840
$^1$H-NMR (D$_2$O, DMSO-d$_6$)δ: 2.3 (6H), 5.9 (2H), 6.9 (2H), 7.5 (2H), 8.4 (2H)

The test results of antiviral activity studies on the compounds of the invention are described in the following experiments 1 and 2 (in vitro antiviral activity).

Experiment 1

Inhibition of viral pathogenic effect

For the assay of cytopathogenic effect (CPE), LLC-MK$_2$ cells were seeded in microtest plates at a concentration of 2.0×10$^4$ cells per well in 0.1 ml of Eagle minimum essential medium (MEM) containing 5% newborn calf serum and 50 μg of kanamycin per ml. After 24 h of growth at 37° C. in a CO$_2$ (5% CO$_2$, 95% air) incubator, the cultures were 80% monolayered and ready for use. Cell cultures in the microtest plates were drained and (except compound toxicity and cell controls) were challenged with 20 μl (100–300 TCID$_{50}$) of enterovirus type 70. The culture incubated for 1 h at 33° C. The virus inoculum was removed and cells were then cultured with MEM containing the compounds to be tested serially diluted. The cell cultures were maintained at 33° C. in a CO$_2$ incubator and examined microscopically at 48, 72, 96 and 120 h after challenge for compound cytotoxicity and virus CPE.

Experiment 2

The test results of Experiment 1 are shown in Table 1. The lowest concentration of a compound that reduced virus CPE and caused morphological cytotoxicity by 50% or more was considered to be the IC$_{50}$ and CD$_{50}$, respectively. Chemotherapeutic index (CI) was obtained by the following formula: CI=CD$_{50}$/ID$_{50}$.

In addition, in plaque reduction assays, these compounds selectively inhibited the plaque formation by human enteroviruses, such as polioviruses (type 1, 2 and 3) echoviruses (type 6, 11 and 25), coxsackieviruses (type A9, A16, B2, B3 and B4) and enterovirus 71.

TABLE 1

| Compound NO | IC$_{50}$ (μg/ml) | CD$_{50}$ (μg/ml) | CI |
|---|---|---|---|
| I | 3.7 | 562.3 | 152 |
| II | 1.8 | 177.8 | 99 |
| III | >100.0 | >100.0 | |
| IV | 27.6 | 1767.8 | 64 |
| V | 1.8 | 562.3 | 311 |
| VI | >100.0 | >100.0 | |
| VII | 1.4 | 176.8 | 126 |
| VIII | >100.0 | >100.0 | |
| IX | 5.5 | 353.6 | 64 |
| X | 0.98 | 353.6 | 362 |
| XI | >100.0 | >100.0 | |
| XII | 3.0 | 707.1 | 239 |

What we claim is:

1. 2-(4-pyridylaminomethyl)-benzimidazole derivatives represented by the following formula:

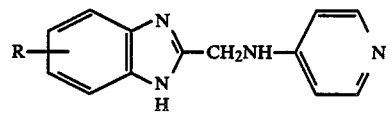

wherein R is a radical selected from the group consisting of hydrogen, 5(6)-chloro, 5(6)-benzoyl, 5(6)-methoxy, 5(6)-methyl, 5(6)-nitro, 5,6-dichloro, 5(6)-amino, 5(6)-trifluoromethyl, 5(6)-ethyl, 4(7)-methyl and 5,6-dimethyl groups.

2. The 2- (4- pyridylaminomethyl)-benzimidazole derivatives of claim 1 composed of tautomeric isomers.

* * * * *